United States Patent
Boatman

(10) Patent No.: US 7,056,337 B2
(45) Date of Patent: Jun. 6, 2006

(54) NATURAL TISSUE STENT

(75) Inventor: Scott E. Boatman, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 10/691,014

(22) Filed: Oct. 21, 2003

(65) Prior Publication Data

US 2005/0085898 A1    Apr. 21, 2005

(51) Int. Cl.
*A61F 2/06*    (2006.01)

(52) U.S. Cl. ............... 623/1.15; 623/1.41; 623/1.44; 623/23.7

(58) Field of Classification Search ..... 623/1.11–23.75
See application file for complete search history.

(56) References Cited

U.S. PATENT DOCUMENTS

| | | | |
|---|---|---|---|
| 5,100,429 A | 3/1992 | Sinofsky et al. | 606/195 |
| 5,197,977 A | 3/1993 | Hoffman, Jr. et al. | 623/1 |
| 5,383,927 A | 1/1995 | De Goicoechea et al. | 623/1 |
| 5,429,634 A * | 7/1995 | Narciso, Jr. | 604/890.1 |
| 5,480,424 A | 1/1996 | Cox | 623/2 |
| 5,681,345 A | 10/1997 | Euteneuer | 606/198 |
| 5,693,085 A | 12/1997 | Buirge et al. | 623/1 |
| RE36,370 E | 11/1999 | Li | 424/443 |
| 6,136,024 A * | 10/2000 | Shimizu | 623/1.47 |
| 6,165,210 A | 12/2000 | Lau et al. | 623/1.12 |
| 6,206,915 B1 | 3/2001 | Fagan et al. | 623/1.42 |
| 6,206,931 B1 * | 3/2001 | Cook et al. | 623/23.75 |
| 6,299,604 B1 | 10/2001 | Ragheb et al. | 604/265 |
| 6,334,872 B1 | 1/2002 | Termin et al. | 623/1.38 |
| 6,358,284 B1 | 3/2002 | Fearnot et al. | 623/23.72 |
| 6,379,379 B1 | 4/2002 | Wang | 623/1.15 |
| 6,379,382 B1 | 4/2002 | Yang | 623/1.42 |
| 6,391,052 B1 | 5/2002 | Buirge et al. | 623/1.47 |
| 6,540,776 B1 | 4/2003 | Sanders Millare et al. | 623/1.15 |
| 6,544,544 B1 | 4/2003 | Hunter et al. | 424/424 |
| 6,572,650 B1 | 6/2003 | Abraham et al. | 623/1.38 |
| 6,613,082 B1 * | 9/2003 | Yang | 623/1.42 |
| 2001/0034550 A1 | 10/2001 | Buirge et al. | 623/1.47 |
| 2001/0039450 A1 | 11/2001 | Pavcnik et al. | 623/1.24 |
| 2001/0041928 A1 | 11/2001 | Pavcnik et al. | 623/1.13 |
| 2001/0053931 A1 | 12/2001 | Hess et al. | 623/1.15 |
| 2002/0062147 A1 | 5/2002 | Yang | 623/1.13 |
| 2002/0065553 A1 | 5/2002 | Weber | 623/1.46 |

(Continued)

FOREIGN PATENT DOCUMENTS

WO    WO 98/22158    5/1998

(Continued)

OTHER PUBLICATIONS

Badylak, Stephen F. et al., "*The Use of Xenogeneic Small Intestinal Submucosa as a Biomaterial for Achille's Tendon Repair in a Dog Model*", Journal of Biomedical Materials Research, vol. 29, pp. 977-985, Aug. 1995.

(Continued)

*Primary Examiner*—Suzette J-J Gherbi
(74) *Attorney, Agent, or Firm*—Brinks Hofer Gilson & Lione

(57) ABSTRACT

A medical implant made from multiple layers of non-synthetic, natural tissues is provided. The medical device includes openings that extend radially through the wall of the medical implant. One advantage of the medical implant is that a synthetic support structure is not needed. As a result, problems associated with implanting a foreign material into a body may be avoided.

10 Claims, 2 Drawing Sheets

U.S. PATENT DOCUMENTS

| | | | |
|---|---|---|---|
| 2002/0099438 A1 | 7/2002 | Furst | 623/1.16 |
| 2002/0123788 A1 | 9/2002 | Sanders Millare et al. | 623/1.13 |
| 2002/0123793 A1* | 9/2002 | Schaldach et al. | 623/1.15 |
| 2002/0183857 A1* | 12/2002 | Yang | 623/23.72 |
| 2003/0009213 A1 | 1/2003 | Yang | 623/1.13 |
| 2003/0040790 A1 | 2/2003 | Furst | 623/1.11 |
| 2003/0060871 A1 | 3/2003 | Hill et al. | 623/1.15 |
| 2003/0065379 A1 | 4/2003 | Babbs et al. | 623/1.13 |
| 2003/0144727 A1 | 7/2003 | Rosenthal et al. | 623/1.15 |
| 2003/0158607 A1* | 8/2003 | Carr et al. | 623/23.72 |
| 2003/0167088 A1* | 9/2003 | Abraham et al. | 623/1.41 |
| 2003/0171824 A1* | 9/2003 | Abraham et al. | 623/23.75 |
| 2004/0002772 A1* | 1/2004 | Sabolinski | 623/23.76 |

FOREIGN PATENT DOCUMENTS

| | | |
|---|---|---|
| WO | WO 01/10355 A1 | 2/2001 |
| WO | WO 2004/026190 A2 | 4/2004 |

OTHER PUBLICATIONS

Cobb, Mark A., M.D. et al., "*Histology After Dural Grafting With Small Intestinal Submucosa*", Surg. Neurol, vol. 46, No. 4, pp. 389-394, Oct. 1996.

Copy of International Search Report from corresponding PCT application No. PCT/US2004/034583 dated Jan. 4, 2005, 3 pages.

* cited by examiner

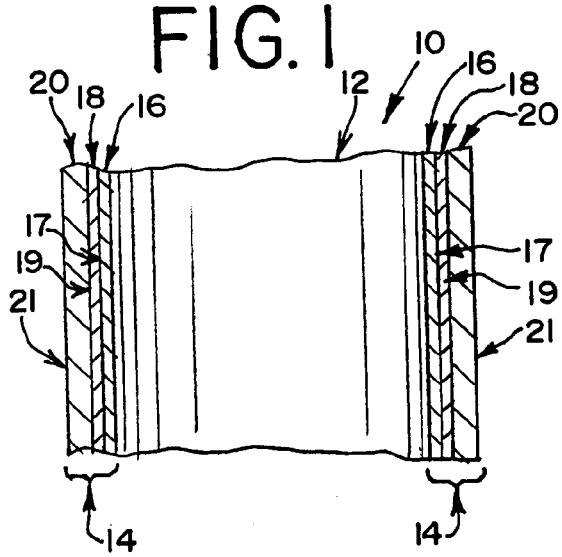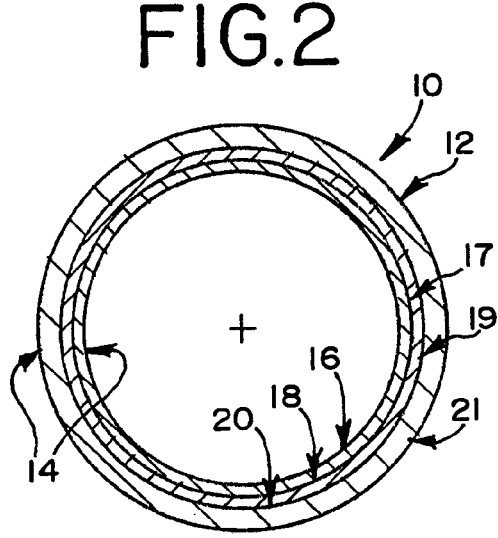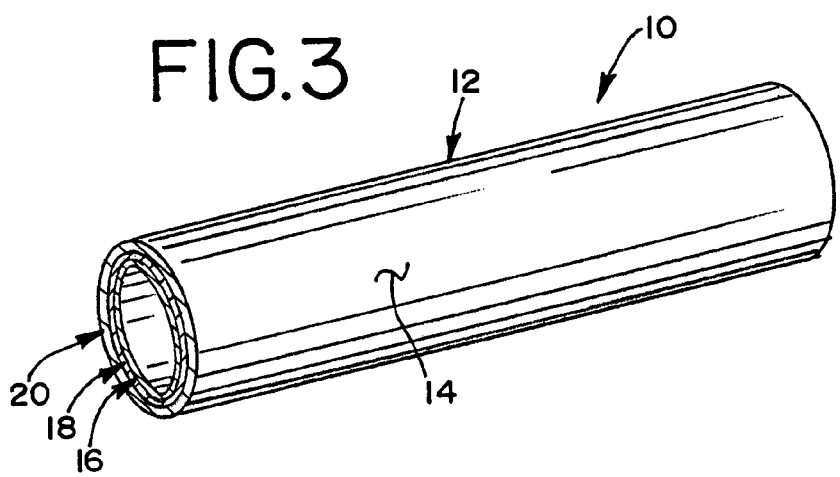

NATURAL TISSUE STENT

BACKGROUND

The present invention relates generally to medical devices and particularly to a medical implant or stent made from natural tissues.

The use of tubular medical implants to treat various organs, such as the vascular system, colon, biliary tract, urinary tract, esophagus, trachea and the like, has become common. Typically, tubular medical implants (e.g., stents, prosthesis, grafts and other such devices) are useful in treating blockages, occlusions, narrowing ailments and other similar problems that restrict flow through a passageway.

One such medical treatment involves the use of an endovascular stent that is implanted in the vascular system. Stents are useful for numerous medical treatments of various vessels throughout the vascular system, including both coronary vessels and peripheral vessels (e.g., carotid, brachial, renal, iliac and femoral). However, the use of stents in coronary vessels has drawn particular attention from the medical community due to the commonality of heart problems caused by stenosis.

Although stenosis (i.e., narrowing of a vessel) may occur for a variety of reasons, one of the most common causes of coronary stenosis results from the buildup of atherosclerotic plaques along the lumen of the vessel. The resulting coronary stenosis restricts blood flow through the vessel, which eventually can lead to a dangerously increased risk of heart attacks.

The medical community has attempted to address coronary stenosis (along with the many other passageway problems that patients suffer from) with various versions of percutaneous transluminal angioplasty ("PTA"). Fundamentally, PTA involves inserting a balloon-tipped catheter into a vessel and threading the catheter to the narrowed portion to be treated. The balloon is then expanded at the narrowed portion by pumping saline through the catheter to the balloon. As a result, the balloon expands, contacts the inner vessel wall, and forces the vessel to dilate. The balloon is then deflated and retracted from the vessel.

One problem that has been encountered with the described version of PTA is restenosis (i.e., a re-narrowing) of the vessel. Restenosis may occur for a variety of reasons, such as collapsing of the vessel wall or regrowth of cellular tissue. For example, restenosis is frequently caused by damage to the vessel lining which occurs during balloon expansion and vessel dilation. As a result of the damage caused to the intima layers of the vessel, the vessel attempts to grow new intima tissue to repair the damage. This tendency of vessels to regrow new tissues is referred to as neointimal hyperplasia. The effect of this response results in a re-narrowing of the vessel. Restenosis however is not completely predictable and may occur either abruptly soon after the PTA procedure or may occur slowly over a longer period of time.

One approach the medical community has tried to overcome the problems with restenosis is to use stents in conjunction with the above-described PTA procedure. Traditionally, stents are made of metal or other synthetic materials, thereby providing a tubular support structure that radially supports the inner wall of the vessel. The most common materials now used in stents are stainless steel (e.g., 316L SS and 304 SS) and Nitinol. Typically, stents are designed with a plurality of openings extending through the support structure in a manner that permits the stent to radially expand from a small diameter to a larger diameter. Thus, when used in conjunction with conventional PTA procedures, the stent is positioned within the portion of the vessel that has been widened by the balloon and is permanently implanted by radially expanding the stent against the inner wall of the vessel. The expectation of this revised PTA procedure is that the support structure of the implanted stent will mechanically prevent the vessel from collapsing back to its original narrowed condition.

Restenosis however can still be a problem even when a stent is used in conjunction with PTA procedures. As discussed above, one problem is neointimal hyperplasia caused by damage to the vessel wall. This can also be a problem when a stent is used. In addition, neointimal hyperplasia can also be caused by the synthetic materials that are usually used in stents. The reason for this problem is that living tissues have a tendency to grow new living tissues around and over foreign objects that are implanted into the body. Thus, despite the mechanical support structure provided by a stent, restenosis remains a problem. One approach that has been offered to address these problems is coating the stent with drugs that are designed to inhibit cellular regrowth. Common examples of such drugs include Paclitaxel, Sirolimus and Everolimus. One problem with conventional drug coatings, however, is that the drug coating is only available at the outer surface of the stent and is quickly released after implantation. Thus, the drug is only effective for a short period of time.

Although stent designs and implantation procedures vary widely, two categories are common.

The first of these two categories may be referred to as balloon-expanding stents. Balloon-expanding stents are generally made from soft ductile materials that plastically deform relatively easily. In the case of stents made from metal, 316L stainless steel which has been annealed is a common choice for these types of stents. One common procedure for implanting a balloon-expanding stent involves mounting the stent circumferentially on the balloon prior to threading the balloon-tipped catheter to the narrowed vessel portion that is to be treated. When the balloon is positioned at the narrowed vessel portion and expanded, the balloon simultaneously dilates the vessel and also radially expands the stent into the dilated portion. The balloon and the catheter are then retracted, leaving the expanded stent permanently implanted at the desired location. Ductile metal lends itself to this type of stent since the stent may be compressed by plastic deformation into a small diameter when mounted onto the balloon. When the balloon is then expanded in the vessel, the stent is once again plastically deformed into a larger diameter to provide the desired radial support structure. Traditionally, balloon-expanding stents have been more commonly used in coronary vessels than in peripheral vessels due to the deformable nature of these stents. One reason for this is that peripheral vessels tend to experience frequent traumas from external sources (e.g., impacts to a person's arms, legs, etc.) which are transmitted through the body's tissues to the vessel. In the case of peripheral vessels, there is an increased risk that an external trauma could cause a balloon-expanding stent to once again plastically deform in unexpected ways with potentially severe and/or catastrophic results. In the case of coronary vessels, however, this risk is minimal since coronary vessels rarely experience traumas transmitted from external sources.

A second common category of stents is referred to as self-expanding stents. Self-expanding stents are generally made of shape memory materials that act like a spring. Typical metals used in these types of stents include Nitinol and 304 stainless steel. A common procedure for implanting a self-expanding stent involves a two-step process. First, the narrowed vessel is dilated with the balloon as described above. Second, the stent is implanted into the dilated vessel portion. To accomplish the stent implantation, the stent is installed on the end of a catheter in a compressed, small diameter state and is retained in the small diameter by inserting the stent into the lumen of the catheter or by other means. The stent is then guided to the balloon-dilated portion and is released from the catheter and allowed to radially spring outward to an expanded diameter until the stent contacts and presses against the vessel wall. Traditionally, self-expanding stents have been more commonly used in peripheral vessels than in coronary vessels due to the shape memory characteristic of the metals used in these stents. One advantage of self-expanding stents for peripheral vessels is that traumas from external sources do not permanently deform the stent. Instead, the stent may temporarily deform during an unusually harsh trauma but will spring back to its expanded state once the trauma is relieved. Self-expanding stents, however, are often considered to be less preferred for coronary vessels as compared to balloon-expanding stents. One reason for this is that balloon-expanding stents can be precisely sized to a particular vessel diameter and shape since the ductile metal that is used can be plastically deformed to a desired size and shape. In contrast, self-expanding stents are designed with a particular expansible range. Thus, after being installed self-expanding stents continue to exert pressure against the vessel wall.

One problem with traditional stents is the metallic and other synthetic materials that are used to make the stents. As mentioned above, the most common material now used to make stents is stainless steel and other similar metals. Other synthetic materials which are sometimes used in stents include various types of polymers. It is well known that the human body is generally resistant to the implantation of foreign materials into the body. For example, in the case of stainless steel (which is used in most stents), it is known that a certain percentage of people are allergic to the nickel contained in stainless steel. Because of the known, general risk of implanting synthetic materials into the human body, the medical community must extensively test any new material or new application before a medical device may be considered safe for permanent implantation. Even then, the response that a particular human body may exhibit to a particular synthetic material can be unpredictable.

Some attempts to address this concern with implanting foreign materials into the human body have relied upon stents made either partly or completely from bioabsorbable/biodegradable materials. Essentially, these materials are polymers that breakdown over time until the original implanted material is either partially or wholly dispersed into the body. Some examples of these types of materials include poly(L-lactic acid), poly(glycolic acid), polycaprolactone and various copolymers thereof. These materials however do not adequately solve the problems with traditional stents and may even cause new problems. For example, these stents do not fully address the concern with implanting synthetic materials into the body, since the bioabsorbable/biodegradable materials that are used are themselves synthetic with potentially unpredictable physiological responses thereto. Moreover, these stents are specifically designed to disintegrate over time into smaller pieces. This may result in a possible embolism if a larger piece unexpectedly breaks off from the stent and passes through the vascular system. Moreover, even when the polymer material degrades into small pieces that avoid the risk of embolisms, the breakup of the polymer material still results in non-natural, synthetic materials being dispersed in an uncontrolled manner throughout the body.

Accordingly, a solution that avoids these and other problems is described more fully below.

SUMMARY

A medical implant is provided which is made from multiple layers of non-synthetic, natural tissues. Openings that extend radially through the wall of the medical implant are also provided. An advantage of the medical implant is that a synthetic support structure is not used. Thus, problems associated with implanting foreign materials into the body are avoided. Additional details and advantages are further described below.

BRIEF DESCRIPTION OF SEVERAL VIEWS OF THE DRAWINGS

The invention may be more fully understood by reading the following description in conjunction with the drawings in which:

FIG. 1 is a side cross-sectional view of a stent;

FIG. 2 is a front cross-sectional view of the stent;

FIG. 3 is a perspective view of the stent; and

DETAILED DESCRIPTION

Figure 4:
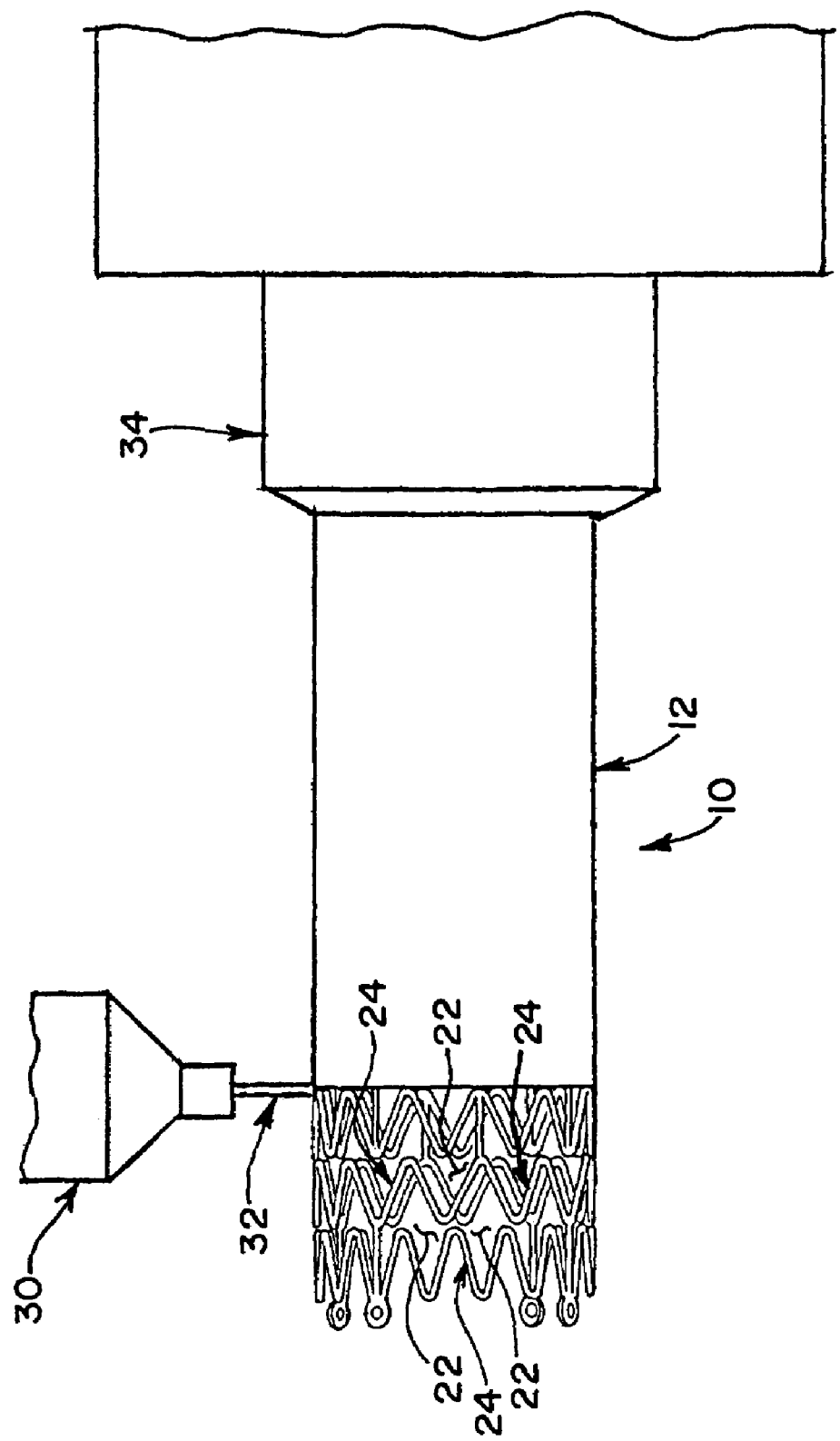
FIG. 4 is a side elevational view of a laser cutting openings into the stent.

Referring now to the figures, a medical implant made from natural tissues is provided. As shown and described, the medical implant is a stent 10 formed from a cannula 12 that is particularly adapted for implantation in the vascular system using percutaneous transluminal angioplasty ("PTA") or other minimally invasive procedures. The concepts shown and described herein however may be useful in numerous other applications to treat human or animal ailments. For example, substantially similar stents, prostheses and/or grafts may also be used to treat various passageway problems in the vascular system, colon, biliary tract, urinary tract, esophagus, trachea and the like.

The cannula 12 includes a tubular wall 14 formed of multiple layers of natural tissues. Herein, the terms "natural" and "non-synthetic" refer to materials that are not man-made from materials that are foreign to human and animal physiology. Synthetic materials that are not encompassed by these terms include metals and artificial polymers. The non-synthetic, natural tissues which may be used with the invention herein are numerous and include various tissues that are harvested, extracted, cultured or otherwise obtained either directly or indirectly from human and animal physiologies.

In the described embodiment, the tubular wall 14 of the cannula 12 is made of three layers of non-synthetic, natural tissues. The inner layer 16 is made from small-intestine submucosa ("SIS") material, which may be obtained from porcine intestine. The middle layer 18 overlays the inner layer 16 and is made from cartilage material. The outer layer 20 overlays the middle layer 18 and is made from SIS material. The multi-layered cannula 12 may be made using a variety of techniques already known to the art. For example, multiple flat sheets of the natural materials may be superimposed and adhered to each other. The multi-layered sheet may then be rolled into a tube and the side edges adhered together in any suitable fashion. Similarly, the multi-layered cannula 12 may also be formed by wrapping the inner layer 16 around a mandrel and successively wrapping the remaining layers 18, 20 on top of the preceding layers. Other methods that may also be used include examples such as coaxial insertion of the layers, casting, spraying, painting and the like. Various non-synthetic, natural tissues may be used depending on the particular needs of an application and the respective advantages or disadvantages of different materials. For example, in the case of the middle layer 18 of cartilage, various types of collagen may also be used as desired. Moreover, the cannula may be formed with a different number of tissue layers than described and shown here.

Drugs may also be incorporated with the cannula 12 for treatment of the implanted region. For example, a drug may be incorporated by infusing the drug into one or more of the layers 16, 18, 20 and/or coating one or more of the layers 16, 18, 20 with the drug. Preferably, Paclitaxel is infused into the inner SIS layer 16 and the outer SIS layer 20. In addition, a first coating 17, second coating 19, and third coating 21 of Paclitaxel is applied to the outer surfaces of the inner layer 16, middle layer 18 and outer layer 20, respectively. Other drugs may be used however and may be incorporated in different combinations than the version shown. For example, the alternative of infusing drugs inside the layers may be used or not used for particular layers as needed. Likewise, the alternative of coating the outside or inside of the layers may also be used or not used for particular layers as needed.

The stent 10 also includes a plurality of openings 22 that extend radially through the multi-layered wall 14 of the cannula 12. Preferably, the openings 22 are formed with a laser 30 that cuts through the wall 14 of the cannula 12 with a laser beam 32. In order to generate a predetermined pattern of openings 22, the cannula 12 is held at one end by a holding fixture 34, and the laser 30 and/or the holding fixture 34 are programmed to move along a predetermined path as is known in the art. The resulting pattern of openings 22 forms a series of struts 24 that separate the openings 22, thereby defining the structure of the stent 10. Since most non-synthetic, natural tissues have similar melting and boiling points, conventional lasers will usually be sufficient to cut the desired openings, with only standard adjustments to the laser cutting parameters being needed. Although laser cutting is the preferred method for forming the openings 22, other methods may also be used. For example, the openings 22 may be formed into the cannula 12 during a casting process. The openings 22 may also be pre-formed into the layers 16, 18, 20 prior to adhering multiple layers together. The openings 22 may also be mechanically cut or punched.

Numerous advantages of the stent are now apparent. A significant advantage of the stent is the absence of a synthetic support structure, such as metal or artificial polymers. This avoids the many known problems associated with implanting foreign materials into the human body. In the particular case of stainless steel, which is now commonly used in traditional stents, the known risk of nickel allergies is completely avoided. In addition, other unknown and unpredictable problems that may be associated with synthetic materials are also avoided.

Thus, in contrast to traditional stents, the support structure is made from non-synthetic, natural tissues instead of metals or synthetic polymers. In the embodiment described above, cartilage is used as the middle layer 18 to provide a support structure. Cartilage is preferred because of its physical properties that make it rigid yet flexible. However, other natural materials may also be used. Preferably, the stent is constructed as a self-expanding stent which may be implanted using techniques similar to conventional procedures. However, depending on the materials used in the stent and the shape and size of the openings, the stent may also be used as a balloon-expanding stent.

The stent also does not have the same problems that bioabsorbable/biodegradable stents suffer from. Unlike bioabsorbable/biodegradable stents which essentially breakdown over time, the described stent does not degrade. Instead, when SIS layers are used as described, the stent will become incorporated into the vessel wall. Thus, the stent does not suffer from the same risk of bioabsorbable/biodegradable stents in which particles may break off and cause embolisms.

Another advantage is that natural tissues with growth factors may be used to encourage cellular growth. In the case of the stent 10 described above, the inner and outer layers 16, 20 of SIS promote cellular growth of the surrounding tissues in the implanted region. As a result, the implanted region of the vessel may accept the natural tissues of the stent and incorporate the stent by making the stent an integral part of the living tissue. The surrounding tissues will then grow into the SIS layers 16, 20, thereby incorporating the stent 10 into the surrounding living tissue. The openings 22 further encourage cellular growth by providing blood flow from the lumen of the vessel through the wall 14 of the cannula 12 to the inner wall of the widened vessel.

Still another advantage is that drugs may be incorporated with the stent in a manner that provides a more continuous, longer drug treatment. As described above, drugs may be infused within the layers 16, 18, 20 and may be coated onto the multiple layers 16, 18, 20. Since the drug is loaded throughout the cannula instead of at only the surface, drugs will continue to be released even after the outer drug coating is gone. Moreover, cell growth into the layers of the stent will further encourage the release of the drugs as the cells infiltrate the layers.

While a preferred embodiment of the invention has been described, it should be understood that the invention is not so limited, and modifications may be made without departing from the invention. The scope of the invention is defined by the appended claims, and all devices that come within the meaning of the claims, either literally or by equivalence, are intended to be embraced therein.

I claim:

1. An expandable stent comprising:
   a cannula formed from a wall, said wall comprising at least a first layer and a second layer, said first layer and said second layer being made of different non-synthetic, natural tissues, said cannula being further characterized by the absence of a synthetic support structure, wherein said second layer comprises a structural layer for supporting said cannula against a vessel wall and said first layer comprises growth factors encouraging said vessel wall to grow within said first layer and said cannula comprises a plurality of openings extending radially through said first layer and said second layer of said wall, said plurality of openings forming a pattern of struts, said cannula being expandable to radially support said vessel wall.

2. The expandable stent according to claim 1, wherein said first layer comprises small-intestine submucosa and wherein said second layer comprises cartilage.

3. The expandable stent according to claim 2, wherein a drug is incorporated with at least one of said first and second layers of said cannula.

4. The expandable stent according to claim 3, wherein said drug is Paclitaxel.

5. The expandable stent according to claim 4, wherein said plurality of openings are formed by cutting through said wall with a laser.

6. The expandable stent according to claim 1, wherein said wall comprises at least a third layer in addition to said first layer and said second layer, said third layer being an outer layer to said second layer and said first layer being an inner layer to said second layer, said third layer comprising small-intestine submucosa.

7. The expandable stent according to claim 6, wherein said first layer comprises small-intestine submucosa and wherein said second layer comprises cartilage.

8. The expandable stent according to claim 7, wherein a drug is incorporated with at least one of said first, second and third layers of said cannula.

9. The expandable stent according to claim 8, wherein said drug is Paclitaxel.

10. The expandable stent according to claim 9, wherein said plurality of openings are formed by cutting through said wall with a laser.

* * * * *